United States Patent [19]

Senaratne et al.

[11] Patent Number: 5,225,588

[45] Date of Patent: Jul. 6, 1993

[54] PROCESS FOR ALKYLATING SALICYLATES WITH POLYALPHAOLEFIN

[75] Inventors: K. Pushpananda A. Senaratne; Patrick S. Bynum, both of Baton Rouge, La.

[73] Assignee: Ethyl Corporation, Richmond, Va.

[21] Appl. No.: 829,712

[22] Filed: Feb. 3, 1992

[51] Int. Cl.$^5$ .............................................. C07C 69/88
[52] U.S. Cl. ........................................ 560/71; 560/67
[58] Field of Search ............................. 560/71, 67

[56] References Cited

U.S. PATENT DOCUMENTS

| | | | |
|---|---|---|---|
| 2,180,008 | 11/1939 | Lincoln et al. | 87/9 |
| 3,382,291 | 5/1968 | Brennan | 260/683.15 |
| 3,808,134 | 4/1974 | Romine | 252/59 |
| 3,812,036 | 5/1974 | Romine | 252/59 |
| 4,011,166 | 3/1977 | Schenach | 252/32.7 E |
| 4,035,308 | 7/1977 | Schenach | 252/59 |
| 4,209,654 | 6/1980 | Booth et al. | 585/465 |
| 4,238,343 | 12/1980 | Pellegrini, Jr. | 585/24 |
| 4,708,809 | 11/1987 | Davis | 252/33.4 |
| 4,933,485 | 6/1990 | Buckley, III | 560/159 |
| 4,962,256 | 10/1990 | Le et al. | 585/467 |
| 5,019,670 | 5/1991 | Le et al. | 585/467 |
| 5,030,785 | 7/1991 | Huss, Jr. et al. | 585/456 |

FOREIGN PATENT DOCUMENTS

| | | |
|---|---|---|
| 0377305 | 7/1990 | European Pat. Off. |
| 2512054 | 3/1982 | France |
| 0639850 | 4/1979 | U.S.S.R. |
| 0581783 | 10/1946 | United Kingdom |
| 0632990 | 12/1949 | United Kingdom |
| 1212462 | 11/1970 | United Kingdom |

*Primary Examiner*—Paul J. Killos
*Attorney, Agent, or Firm*—David M. Bunnell

[57] ABSTRACT

Hydroxybenzoates such as methylsalicylate are alkylated by reacting a hydroxybenzoate with a polyalphaolefin in the presence of a catalytic amount of $SnCl_4$.

16 Claims, No Drawings

PROCESS FOR ALKYLATING SALICYLATES WITH POLYALPHAOLEFIN

This invention relates generally to the alkylation of hydroxybenzoates to form compounds which are useful, for example, as diesel lubricant detergents and more specifically to a process for alkylating salicylates with polyalphaolefins.

Alkyl salicylates are known to be excellent diesel lubricant detergents. Alpha-olefin oligomers often referred to in the art as "polyalphaolefins" (PAO's), are known to be excellent synthetic lubricants which have improved low temperature properties compared with mineral oils and other synthetic oils. The polyalphaolefins are prepared by oligomerizing alpha-olefins having from about 8 to 20 carbon atoms and, especially 1-decene, using Friedel Crafts catalysts such as $AlCl_3$ or $BF_3$ with a promoter such as water or an alcohol. The oligomers are complex mixtures of highly branched tri- and tetrasubstituted internal olefins. We believe that the hindered nature of these olefin bonds makes the alkylation of the phenyl ring of hydroxybenzoates, such as salicylates, with PAO's, difficult, and with most alkylation catalysts results in negligible yields at ambient temperatures and poor yields even under forcing conditions such as high temperatures and longer reaction time. We have discovered a process which not only provides acceptable yields of alkylated hydroxybenzoates, but surprisingly, is even more effective at ambient temperatures than at elevated temperatures.

In accordance with this invention there is provided a process for alkylating a hydroxybenzoate, said process comprising reacting a hydroxybenzoate with an unsaturated polyalphaolefin in the presence of a catalytic amount of $SnCl_4$ so as to alkylate the phenyl ring of the hydroxybenzoate with said polyalphaolefin.

Also provided is an alkylated hydroxybenzoate which can be prepared by the process comprising reacting a hydroxybenzoate with an unsaturated polyalphaolefin in the presence of a catalytic amount of $SnCl_4$.

Yields are improved if the reaction is carried out in a halogenated solvent.

The preparation of PAO's using Friedel-Crafts catalysts such as boron trifluoride ($BF_3$) as disclosed in U.S. Pat. No. 3,149,178 is well known. Optimum lubricant properties are obtained starting with 1-decene although mixtures of alpha-olefins have been used cf. U.S. Pat. No. 3,330,883. Pure $BF_3$ is not an effective oligomerization catalyst. A small amount of polar compound is necessary as a promoter. U.S. Pat. No. 3,382,291 describes the use of alcohol promoters such as decanol. Alcohols containing about 1-8 carbon atoms such as methanol, ethanol, isopropanol, n-propanol, n-butanol, isobutanol, n-hexanol and n-octanol can also be used. Other promoters include, for example, mordenite (hydrogen form), organic acids (e.g. carboxylic acids such as acetic acid, valeric acid, caproic acid or other fatty acids, sulfonic acids and the like), polyhydric alcohols (e.g. glycol, glycerol and the like), ketones (e.g. acetone, methylethyl ketone and the like), aldehydes (e.g. butyraldehyde and the like), acid anhydrides (e.g. acetic anhydride and the like), dialkyl ethers (e.g. diethyl ether, di-n-butyl ether and the like, dioxane, glycol ethers (e.g. ethylene glycol monomethylether (w-methoxyethanol), ethylene glycol monoethylether, diethylene glycol diisobutyl-ether, propylene glycol monoethylether and the like), and fatty acid alkyl esters (e.g. methyl acetate, ethyl propionate, ethyl valerate, methyl oleate and the like). The ethers, esters, anhydrides, ketones and aldehydes provide good promotion properties when combined with other promoters which have an active proton e.g. water or alcohols.

The amount of promoter is an amount that causes the $BF_3$ to act as an oligomerization catalyst. A useful range is about 0.1 to 3.0 weight percent promotor based on alpha-olefin. $BF_3$ is usually used in molar excess to the promotor.

Methods of conducting a $BF_3$ catalyzed oligomerization process are well-known. In one mode, $BF_3$ is merely bubbled through the alpha-olefin reaction mixture containing a promoter during the oligomerization. Generally, the process is conducted under $BF_3$ pressure. A useful pressure is about 1–100 psig and especially 5–50 psig.

Alpha-olefins most useful in preparing synthetic base oils are mainly linear terminal olefins containing about 8 to 20 and, preferably 8 to 12 carbon atoms such as 1-octene, 1-decene, 1-dodecene and the like including mixtures thereof. The most preferred alpha-olefin is 1-decene or an olefin mixture containing mainly, for example, at least 75 weight percent 1-decene.

Generally, reaction temperatures range from about $-10°$ to $200°$ C. and especially from about $20°-50°$ C.

The oligomer products are mixtures which include varying amounts of dimer, trimer, tetramer, pentamer and higher oligomers of the monomer, depending upon the particular alpha-olefin, catalyst and reaction conditions. The products are unsaturated and usually have viscosities ranging from about 1 to 100 cSt or higher and especially from about 1 to 15 cSt at $100°$ C.

The product viscosity can be further adjusted by either removing or adding higher or lower oligomers to provide a composition having the desired viscosity for a particular application.

According to the process of the invention the unhydrogenated PAO's which comprise tri- and tetrasubstituted olefins and, preferably, those containing 16 to 50 carbon atoms, including mixtures thereof, are reacted with from about 0.5 to 5 moles per mole of PAO of a hydroxybenzoate.

Hydroxybenzoates for use in the invention are monohydroxyalkylbenzoates where the alkyl group has from 1 to about 12 carbon atoms e.g. methyl, ethyl, and straight and branched chain isomers of propyl, butyl, pentyl, hexyl and the like. Preferred are alkylsalicylates and especially methylsalicylate.

The reaction is catalyzed by $SnCl_4$ in catalytic amounts which generally range from about 0.1 to 2 moles per mole of PAO.

The reaction is preferably carried out in an organic solvent and we have found that using a halogenated hydrocarbon solvent provides improved yields. Suitable halogenated hydrocarbon solvents include, but are not limited to, dichloroethane, methylene chloride, methylene dibromide, ethylene dibromide, and the like. The solvent is generally used in amounts of up to about 75 percent by volume of the total reaction mixture.

The reaction temperature is selected to provide optimum yields and generally ranges from about $0°$ to $100°$ C. Ambient temperatures of about $20°$ to $30°$ C. have surprisingly been found to provide the best yields of PAO - methylsalicylate product especially in view of the fact that to obtain any measurable yield of product with catalysts other than $SnCl_4$ requires high temperatures.

The invention is further illustrated by, but is not intended to be limited to, the following examples.

EXAMPLE 1

Approximately 20 ml of 1,2-dichloroethane were added to 4.6 ml (36.5 mmol) of methylsalioylate in a flask under a nitroqen purge. 2.1 ml (17.8 mmol) of tin tetrachloride were added to the flask, followed by 5.0 g (17.8 mmol) of $C_{20}H_{40}$ which was a decene dimer (2 cSt PAO) obtained by the $BF_3$-alcohol promoted oligomerization of 1-decene. The solution was stirred at room temperature for eighteen hours. Gas chromatography showed a product yield of 41%. The solution was washed with water, 20% sodium bicarbonate solution, and ether. The organic layer was separated, dried over magnesium sulfate and filtered. Finally, excess solvent was removed by a rotoevaporator. GC/MS showed that the product had a molecular weight of 432 g/mol.

EXAMPLE 2

A solution of 2 cSt PAO (1-decene dimer as in Example 1) (5.0 g, 17.8 mmol), methyl salicylate (5.4 g, 35.6 mmol), 1,2-dichloroethane (20 mL), and $SnCl_4$ (4.6 g, 17.8 mmol) was stirred at 25° C. for 18 hours. Gas chromatography showed a product yield of 41%. Excess methyl salicylate (2.7 g, 17.8 mmol) was added to the solution. After stirring at room temperature for 24 hours, the yield had improved to 47%. The solution was then heated for one hour at reflux. Product yield dropped to 27%.

EXAMPLES 3 TO 13

The general procedure of Example 2 was followed using the reactants and reaction parameters shown in Table 1 below. The results show the advantage of using a chlorinated solvent and ambient temperatures. The methyl-4-hydroxybenzoate was very difficult to alkylate even under optimum conditions.

one minute. The solution was stirred at 25° C. for 18 hours. GC showed only a trace of product. The solution was then stirred at reflux (83° C.) for two hours. Gas chromatography showed a yield of 14%.

Comparison 2. $BF_3$ gas was bubbled through a solution of 2 cSt PAO (5.0 g, 17.8 mmol), butyl salicylate (3.8 g, 19.6 mmol), and 1,2-dichloroethane (40 mL) for one minute. The solution was stirred at 25° C. for 18 hours. GC showed only a trace of product. The solution was heated to reflux (83° C.) for two hours. Gas chromatography showed a product yield of 16%.

Comparison 3. $BF_3$ gas was bubbled through a solution of 2 cSt PAO (5.0 g, 17.8 mmol), methyl salicylate (3.0 g, 19.6 mmol), methanol (0.05 mL), and 1,2-dichloroethane (20 mL) for one minute. The solution was stirred at 25° C. for 18 hours. GC showed no product yield. The solution was stirred at reflux (83° C.) for four hours. Gas chromatography showed a yield of 15%.

Comparison 4. A solution of 2 cSt pAO (5.0 g, 17.8 mmol), methyl salicylate (3.0 g, 19.6 mmol), 1,2-dichloroethane (20 mL), and $AlCl_3$ catalyst (0.12 g, 0.89 mmol) was stirred at 25° C. for 18 hours. GC showed no product yield. The solution was then stirred at reflux (83° C.) for 1.5 hours. GC still showed no product formation.

Comparison 5. A solution of 2 cSt PAO (5.0 g, 17.8 mmol), methyl salicylate (8.1g, 53.4 mmol), 1,2-dichloroethane (20 mL), and $CF_3CO_2H$ catalyst (2.0 g, 17.8 mmol) were stirred at 25° C. for 18 hours. Gas chromatography showed no product yield. The solution was stirred for one hour at 90° C. Gas chromatography still indicated no product formation.

What is claimed is:

1. A process for alkylating a hydroxybenzoate said process comprising reacting a hydroxybenzoate with an unsaturated polyalphaolefin in the presence of a catalytic amount of $SnCl_4$ so as to alkylate the phenyl ring of the hydroxybenzoate with said polyalphaolefin.

2. The process of claim 1 wherein said reaction is carried out in a halocarbon solvent.

3. The process of claim 1 wherein said unsaturated polyalphaolefin is prepared by oligomerizing an alpha-olefin having from about 8 to 20 carbon atoms using a Friedel-Crafts catalyst.

4. The process of claim 3 wherein said Friedel-Crafts catalyst is $BF_3$ and a promotor.

5. The process of claim 3 wherein said hydroxy-benzoate is an alkylsalicylate.

TABLE 1

| Example | Olefin A | Salicylate B | Catalyst C | Mole Ratio A:B:C | Solvent | Temp. (°C.) | Time (Hrs.) | Yield % |
|---|---|---|---|---|---|---|---|---|
| 3 | 2 cSt PAO | Methyl salicylate | $SnCl_4$ | 1:1:0.5 | Dichloroethane | 25 | 18 | 13 |
| 4 | 2 cSt PAO | Methyl salicylate | $SnCl_4$ | 1:1:0.5 | Dichloroethane | 83 | 2 | 13 |
| 5 | 2 cSt PAO | Methyl salicylate | $SnCl_4$ | 1:1:0.5 | Dichloroethane | 25 | 3 | 36 |
| 6 | 2 cSt PAO | Methyl salicylate | $SnCl_4$ | 1:3:1 | Dichloroethane | 83 | 1 | 27 |
| 7 | 2 cSt PAO | Methyl salicylate | $SnCl_4$ | 1:3:1 | Dichloroethane | 0 | 4 | 17 |
| 8 | 2 cSt PAO | Methyl salicylate | $SnCl_4$ | 1:3:1 | Heptane | 25 | 18 | 5 |
| 9 | 2 cSt PAO | Methyl Salicylate | $SnCl_4$ | 1:3:1 | Heptane | 83 | 4 | 6 |
| 10 | 2 cSt PAO | Me.3-hydroxy-benzoate | $SnCl_4$ | 1:2:1 | Dichloroethane | 25 | 18 | 25 |
| 11 | 2 cSt PAO | Me.3-hydroxy-benzoate | $SnCl_4$ | 1:2:1 | Dichloroethane | 83 | 1 | 0 |
| 12 | 2 cSt PAO | Me.4-hydroxy-benzoate | $SnCl_4$ | 1:2:1 | Dichloroethane | 25 | 18 | 2 |
| 13 | 2 cSt PAO | Me.4-hydroxy-benzoate | $SnCl_4$ | 1:2:1 | Dichloroethane | 83 | 1 | 5 |

As a comparison when other alkylating catalysts were used, the maximum yield was about 16% at reflux temperature 83° C. At 25° C. GC showed at most only a trace amount of product. Catalysts used included $BF_3/CH_3OH$, $BF_3/H_2O$, $BF_3$-$Et_2O$, triethyl-aluminum, $CF_3CO_2H$, $AlCl_3$, $H_2SO_4$ (no solvent) and $TiCl_4$. Only the $BF_3$ and $BF_3/CH_3OH$ catalyzed reactions provided any measurable amount of product under the reaction conditions illustrated below.

Comparison 1. $BF_3$ gas was bubbled through a solution of 2 cSt PAO (5.0 g, 17.8 mmol), methyl salicylate (3.0 g, 19.6 mmol), and 1,2-dichloroethane (40 mL) for 6. The process of claim 5 wherein said alkyl-salicylate is methyl salicylate.

7. The process of claim 6 wherein said unsaturated polyalphaolefin is a decene dimer and said reaction is carried out in a halocarbon solvent.

8. The process of claim 7 wherein the reaction temperature is from about 20° to 30° C.

9. An alkylated hydroxybenzoate comprising a hydroxybenzoate whose phenyl ring has been alkylated with an unsaturated polyalphaolefin oil, which oil is an oligomer of an α-olefin having from about 8 to 20 carbon atoms.

10. The alkylated hydroxybenzoate of claim 9 wherein said unsaturated polyalphaolefin oil has a viscosity of from about 1 to 100 cSt at 100° C.

11. The alkylated hydroxybenzoate of claim 10 wherein said unsaturated polyalphaolefin oil has a viscosity of from about 1 to 15 cSt at 100° C.

12. The alkylated hydroxybenzoate of claim 11 wherein said unsaturated polyalphaolefin oil is prepared using a Friedel-Crafts catalyst.

13. The alkylated hydroxybenzoate of claim 12 wherein said Friedel-Crafts catalyst is $BF_3$ and a promotor.

14. The alkylated hydroxybenzoate of claim 9 wherein said hydroxybenzoate is an alkylsalicylate.

15. The alkylated hydroxybenzoate of claim 14 wherein said alkylsalicylate is methyl salicylate.

16. The alkylated hydroxybenzoate of claim 15 wherein said unsaturated polyalphaolefin oil is a decene dimer.

* * * * *